(12) United States Patent
Mannion et al.

(10) Patent No.: US 12,721,642 B2
(45) Date of Patent: Sep. 1, 2026

(54) EXTENDABLE URETEROSCOPE SHEATH

(71) Applicant: C. R. Bard, Inc., Franklin Lakes, NJ (US)

(72) Inventors: Paul T. Mannion, Eliot, ME (US); Melody M. H. Kuroda, Durham, NC (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 486 days.

(21) Appl. No.: 17/728,534

(22) Filed: Apr. 25, 2022

(65) Prior Publication Data

US 2022/0354520 A1 Nov. 10, 2022

Related U.S. Application Data

(60) Provisional application No. 63/185,265, filed on May 6, 2021.

(51) Int. Cl.

| | |
|---|---|
| ***A61B 17/22*** | (2006.01) |
| ***A61B 1/00*** | (2006.01) |
| ***A61B 1/018*** | (2006.01) |
| ***A61B 1/307*** | (2006.01) |
| ***A61B 18/00*** | (2006.01) |
| ***A61B 18/24*** | (2006.01) |
| ***A61M 25/00*** | (2006.01) |

(52) U.S. Cl.

CPC .... *A61B 17/22031* (2013.01); *A61B 1/00135* (2013.01); *A61B 1/018* (2013.01); *A61B 1/307* (2013.01); *A61B 18/245* (2013.01); *A61B 2018/00511* (2013.01); *A61M 25/0074* (2013.01)

(58) Field of Classification Search

CPC ............ A61B 1/00135; A61B 1/00089; A61B 17/22031; A61B 2017/00278

See application file for complete search history.

(56) References Cited

U.S. PATENT DOCUMENTS

| | | | | |
|---|---|---|---|---|
| 2016/0066934 A1* | 3/2016 | Antonelli | ............. | A61B 17/221 606/127 |
| 2016/0374700 A1* | 12/2016 | Olden | ................ | A61B 1/00137 606/106 |
| 2021/0177244 A1* | 6/2021 | Weitzner | ............ | A61B 1/00066 |

* cited by examiner

*Primary Examiner* — Alexandra L Newton

(74) *Attorney, Agent, or Firm* — Rutan & Tucker LLP

(57) ABSTRACT

A sheath assembly for use with an endoscope and an endoscope that includes the sheath assembly. The sheath assembly can include an elongate tubular sheath configured to thread onto a shaft of the endoscope. The sheath can include a pliable segment at a distal end of the sheath, and a tensile filament extends along a circumference of the pliable segment. The tensile filament can form a cinching loop at a distal end of the pliable segment. The sheath can be displaceable along the endoscope between a retracted position and an extended position. The pliable segment can extend distally beyond a distal end of the endoscope to form a chamber, and proximal displacement of the tensile filament tightens the cinching loop to convert the chamber from an open configuration to a closed configuration.

17 Claims, 7 Drawing Sheets

200
211
212
23
20B
210
20
213
214
22
216
21
20A 225A
212B
211
213
212
226
212A
225

214
210A
20
216
216A
228
226
226
225
227
227A

EXTENDABLE URETEROSCOPE SHEATH

PRIORITY

This application claims the benefit of priority to U.S. Provisional Application No. 63/185,265, filed May 6, 2021, which is incorporated by reference in its entirety into this application.

BACKGROUND

Kidney stones may be treated in various ways. Small kidney stones may pass through the urinary tract without treatment. Larger kidney stones or kidney stones that block the urinary tract may need to be removed via a medical procedure. Laser lithotripsy is a procedure to remove a calculus (e.g., a kidney stone) from the urinary tract of the patient. Laser lithotripsy includes inserting a laser optical fiber through the urinary tract to the calculus. The laser is then activated to break the calculus into small pieces that can be passed naturally by the patient or removed by a retrieval instrument. A typical procedure includes inserting an endoscope (i.e., a ureteroscope) through the urethra, bladder, ureter and if necessary, into the kidney so that a distal tip of the scope is positioned adjacent the calculus. The laser optical fiber is inserted through a working channel of the ureteroscope to the calculus. The laser is then activated to break up the calculus.

With the calculus broken up, the laser optical fiber is removed from the working channel so that a retrieval device including a basket may inserted through the working channel to the calculus site. The calculus pieces are then retrieved within the basket. The retrieval device is then removed from the patient along with the endoscope. A camera of the endoscope may be utilized to guide the endoscope to the calculus site, to detect the calculus, to break up the calculus with the laser, and to gather the calculus pieces into the basket.

Removing the laser optic fiber from the working channel so that a separate retrieval device may be inserted requires procedure time clinician and the patient. Use of the retrieval device also adds cost to the procedure. A ureteroscope having a calculus removal capability would provide an advantage to the clinician and the patient.

SUMMARY

Briefly summarized, disclosed herein are a sheath assembly for use with an endoscope and an endoscope that includes the sheath assembly. The sheath assembly includes an elongate tubular sheath configured to thread onto a shaft of the endoscope. The sheath includes a pliable segment at a distal end of the sheath, and a tensile filament extends along a circumference of the pliable segment. The tensile filament forms a cinching loop at a distal end of the pliable segment, and the tensile filament further extends proximally along the sheath. The sheath is displaceable along the endoscope between a retracted position and an extended position. The pliable segment extends distally beyond a distal end of the endoscope in the extended position to form a chamber, and proximal displacement of the tensile filament tightens the cinching loop to convert the chamber from an open configuration to a closed configuration.

The endoscope may be a ureteroscope and the sheath assembly may be configured for insertion into a kidney of a patient body. The sheath assembly may also be configured for the removal of a calculus or portions thereof from a patient. The sheath assembly may also be configured for removal of the calculus while a laser optical fiber is disposed within a working channel of the endoscope.

The tensile filament may extend proximally along the shaft of the endoscope toward a handle of the endoscope, and a loop portion of the tensile filament may be at least partially disposed within an annular sleeve of the pliable segment. A proximal portion of the tensile filament may be disposed within a longitudinal lumen of the sheath. The tensile filament may include a pre-formed loop shape, and the tensile filament may include a metallic wire. The sheath may extend proximally along the shaft of the endoscope toward a handle of the endoscope.

The sheath assembly may include an actuator operatively coupled with the tensile filament, and the actuator may be configured for manual manipulation between a first position and a second position, such that the chamber is disposed in the open configuration when the actuator is in the first position, and the chamber is converted to the closed configuration when the actuator is manipulated to the second position. In some embodiments, the actuator is a slidable actuator configured for manual manipulation between a distal first position and a proximal second position.

The sheath includes an elongate main segment extending distally away from a proximal end of the sheath, and the main segment may be configured to flex in accordance with the shaft of the endoscope. In some embodiments, the actuator is coupled with the main segment.

The sheath may also include an articulating segment disposed between the main segment and the pliable segment, wherein the articulating segment is configured to articulate in accordance with an articulating section of the shaft of the endoscope.

Also disclosed herein is an endoscope including an elongate flexible shaft coupled with a handle at the proximal end of the shaft and a tubular sheath slidably coupled with the shaft. The sheath includes a pliable segment at a distal end of the sheath, and a tensile filament extends along a circumference of the pliable segment to form a cinching loop at a distal end of the pliable segment. The tensile filament further extends proximally along the sheath. The sheath is displaceable along the endoscope between a retracted position and an extended position. The pliable segment extends distally beyond a distal end of the endoscope in the extended position to form a chamber, and proximal displacement of the tensile filament tightens the cinching loop to convert the chamber from an open configuration to a closed configuration.

The sheath is configured for insertion into a kidney of a patient body and the sheath is configured for the removal of a calculus or portions thereof from a patient. In some embodiments, the sheath is configured for the removal of a calculus or portions thereof while a laser optical fiber is disposed within a working channel of the endoscope.

The handle may include a sheath actuator operatively coupled with the sheath via a wire extending along the shaft, and manipulation of the sheath actuator displaces the sheath between the retracted position and the extended position. In some embodiments, the sheath actuator is configured for manual manipulation between a proximal first position consistent with the proximal position of the sheath and a distal second position consistent with the distal position of the sheath. In some embodiments, the wire is disposed within a wire lumen of the shaft.

The tensile filament extends proximally along the shaft to the handle and the tensile filament may be disposed within a filament lumen of the shaft. A loop portion of the tensile filament may be at least partially disposed within an annular sleeve of the pliable segment and the tensile filament may be disposed within a longitudinal lumen of the sheath. The tensile filament may include a pre-formed loop shape and the tensile filament may include a metallic wire.

The handle may include a cinching actuator operatively coupled with the tensile filament, and the cinching actuator may be configured for manual manipulation between a first position and a second position, such that the chamber is disposed in the open configuration when the actuator is in the first position, and the chamber is converted to the closed configuration when the actuator is manipulated to the second position. The cinching actuator may be a slidable actuator configured for manual manipulation between a distal first position and a proximal second position.

Also disclosed herein is a method for removing a calculus from a patient body. The method includes inserting an endoscope within a patient body, the endoscope including a working channel extending along an elongate shaft of the endoscope, and positioning a distal end of the endoscope adjacent the calculus. The method further includes breaking up the calculus into calculus pieces, extending a sheath distally along the shaft to form an open-ended chamber at a distal end of the endoscope, gathering one or more calculus pieces into the chamber, and encapsulating the calculus pieces therein. The method further includes proximally displacing a tensile filament along the shaft, wherein the tensile filament forms a cinching loop along a circumference of a distal end of the chamber, and displacing the tensile filament tightens the cinching loop to close off the chamber. The method further includes withdrawing the endoscope from the patient body.

In some embodiments, the method includes inserting a laser optical fiber within the working channel of the endoscope. The method may further include applying a suction at a proximal end of the working channel to urge the calculus pieces into the chamber. In some embodiments, withdrawing the endoscope from the patient body is performed with the laser optical fiber disposed within the working channel.

These and other features of the concepts provided herein will become more apparent to those of skill in the art in view of the accompanying drawings and following description, which disclose particular embodiments of such concepts in greater detail.

BRIEF DESCRIPTION OF THE DRAWINGS

Embodiments of the disclosure are illustrated by way of example and not by way of limitation in the figures of the accompanying drawings, in which like references indicate similar elements and in which.

DETAILED DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

The directional terms "proximal" and "distal" are used herein to refer to opposite locations on a device or instrument. The proximal end of the device is defined as the end of the device closest to the end-user when the device is in use by the end-user. The distal end is the end opposite the proximal end, along the longitudinal direction of the device, or the end furthest from the end-user.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Figure 1A:
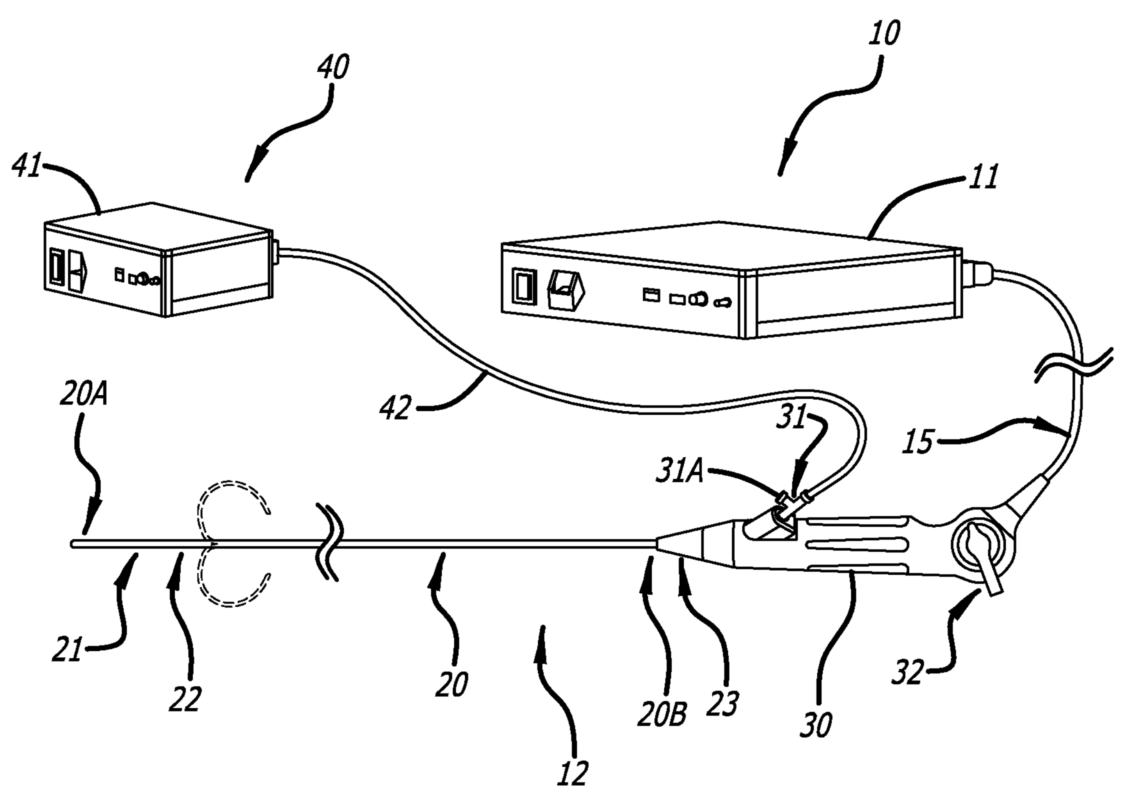
FIG. 1A is an illustration of a current embodiment of an endoscope system including an endoscope coupled with a fiber optic laser system.

FIG. 1A is an illustration of a current embodiment of an endoscope system (system) 10. The system 10 includes an endoscope 12, which may be a ureteroscope, coupled with a video control module 11 via a cable 15. A fiber optic laser system 40 including a laser control module 41 and laser optical fiber 42 is also shown. The laser optical fiber 42 is inserted into the endoscope 12 via an access port 31. The access port 31 includes a fluid port 31A in fluid communication with the access port 31.

The endoscope 12 includes a flexible elongate shaft 20 defining a rigid distal tip 21 at a distal end 20A. The shaft 20 is attached to a handle 30 via a stain relief 23 at a proximal end 20B. The shaft 20 includes an articulating section 22 configured to articulate in opposing directions as shown. The articulating section 22 is operatively coupled with an articulation lever 32 disposed on the handle 30. The articulating section 22 is configured to articulate in accordance with actuation of the articulation lever 32.

Figure 1B:
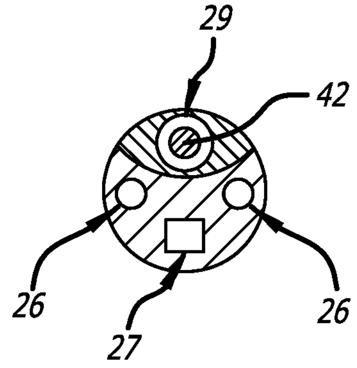
FIG. 1B is an end view of the endoscope of FIG. 1A.

FIG. 1B is a distal end view of the shaft 20. As shown, the endoscope 12 includes one or more light sources 26 configured to provide illumination for a video camera 27. A working channel 29 extends through the shaft 20 between the distal end 20A and the access port 31. The laser optical fiber 42 may be disposed within the working channel 29 so that a distal end of the laser optical fiber 42 is positioned adjacent the distal end 20A of the shaft 20.

Methods of using the endoscope system 10 may include the following steps or processes. The clinician may couple the endoscope 12 with the fiber optic laser system 40 by inserting the laser optical fiber 42 into the working channel 29 of the endoscope 12. In some instances, a distal end of the laser optical fiber 42 is positioned adjacent the distal end 20A of the shaft 20. The clinician may insert the shaft 20 of the endoscope 12 through the urethra and the bladder of a patient. In some instances, the clinician may insert the shaft 20 of the endoscope 12 into the ureter and kidney. During insertion, the clinician may actuate the articulation lever 32 to articulate the articulation section 22 of the shaft 20 to steer the rigid distal tip 21 toward the desired location within the patient. In doing so, the clinician may observe video images acquired by the video camera 27 to help guide the rigid distal tip 21. The clinician may also utilize the video camera to visually detect a calculus to be removed. Upon detection, the clinician may activate the laser fiber optic laser system 40 to break up the calculus into small pieces for removal.

In some current embodiments, the clinician may remove the laser optical fiber 42 from the working channel 29. The clinician may then insert a calculus retrieval device (e.g., a basket; not shown) into the working channel 29 so that the basket extends beyond the distal end 20A of the shaft 20. The clinician may then activate the basket to ensnare the pieces of the calculus. The clinician may then remove the endoscope 12 and the basket containing the calculus pieces from the patient.

Figures 2A, 2B, 2C:
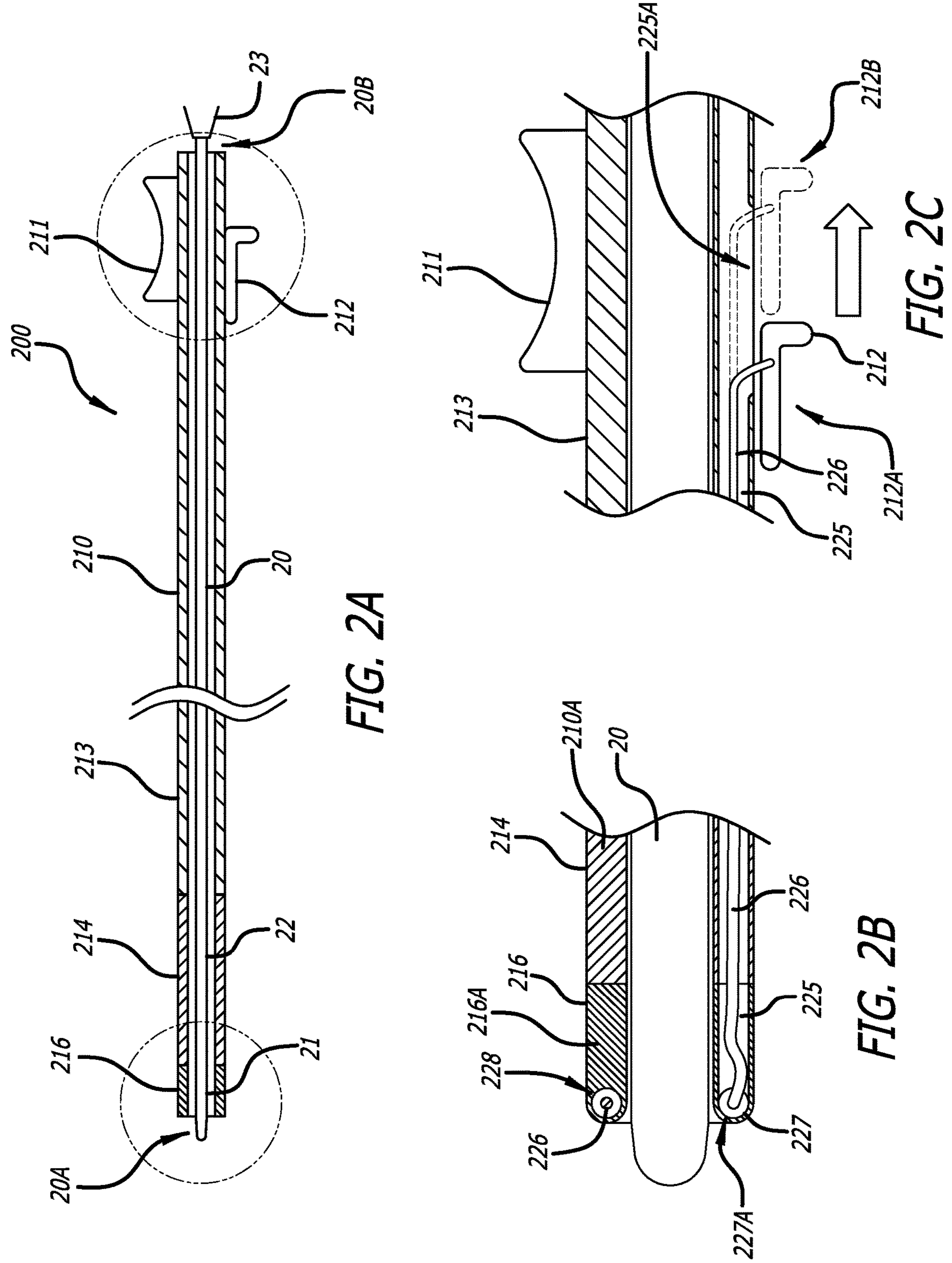
FIG. 2A is a cross-sectional side view of a sheath assembly shown coupled with a shaft of the endoscope of FIG. 1A, in accordance with some embodiments.
FIG. 2B is a cross-sectional detail view of a distal portion of the sheath assembly of FIG. 2A, in accordance with some embodiments.
FIG. 2C is a cross-sectional detail view of a proximal portion of the sheath assembly of FIG. 2A, in accordance with some embodiments.

FIGS. 2A-2E illustrate a first embodiment of a sheath assembly 200 configured for placement on a shaft of an endoscope such as the shaft 20 of the endoscope 12 of FIGS. 1A, 1B or any other type of endoscope. Portions of the endoscope 12 are shown in FIGS. 2A-2E for reference. With reference to FIG. 2A, the sheath assembly 200 is configured for threading onto the shaft 20 before use of the endoscope 12. The sheath 200 is configured for insertion into the patient. In some embodiments, the sheath 200 is configured for insertion into a ureter and/or kidney of a patient. The sheath assembly 200 may extend along a length of the shaft 20, and in some embodiments, sheath assembly 200 may extend between the distal end 20A and the proximal end 20B. In some embodiments, the sheath assembly 200 may be provided separate from the endoscope 12 so that the clinician may thread the sheath assembly 200 onto the endoscope 12 prior to use. In other embodiments, the endoscope 12 may be provided with the sheath assembly 200 pre-coupled therewith.

The sheath assembly 200 includes a sheath 210 shown extending over the shaft 20. The sheath 210 includes a main segment 213, an articulating segment 214, and a pliable segment 216. The main segment 213 extends distally to the articulating segment 214 and the articulating segment 214 extends between the main segment 213 and the pliable segment 216. The sheath assembly 200 is configured to slide relative to the shaft 20 during use as further described below.

The main segment 213 is configured to flex in a manner consistent with the flexibility of the shaft 20 so that the flexibility of the shaft 20 is not appreciably altered by the sheath 210. Similarly, the articulating segment 214 of the sheath 210 is configured to articulate consistent with the articulating section 22 of the shaft 20. In some embodiments, the articulating segment 214 may be include features (e.g., notches) to define a flexibility of the articulating segment 214 in opposing directions consistent the articulating section 22. The main segment 213 and the articulating segment 214 may be formed of a medical grade plastic material such as polypropylene, polyethylene, polytetrafluoroethylene, or any other suitable plastic material.

The pliable segment 216 is configured to deform in contact with body tissue so as to not cause injury to the patient during use. The pliable segment 216 may be formed of any medical grade pliable material such as silicone, ethylene propylene diene monomer, rubber, plasticized polyvinyl chloride, or any other suitable plastic or elastomeric material. In some embodiments, the pliable segment 216 may include structural elements such as longitudinal ribs, corrugations, bellows, or any other structural elements that may help define the shape and functionality of the pliable segment 216.

The sheath assembly 200 further includes a sheath handle 211 attached to the sheath 210 adjacent a proximal end of the sheath 210. The sheath handle 211 is configured for manipulation of the sheath 210 by the clinician. More specifically, the sheath handle 211 is configured for longitudinal displacement of sheath 210 with respect to the shaft 20 between a retracted position and an extended position.

FIG. 2B is a cross-sectional detail view of a distal portion of the sheath assembly 200, and FIG. 2C is a cross-sectional detail view of a proximal portion of the sheath assembly 200. With reference to FIGS. 2B and 2C, the sheath assembly 200 includes a tensile filament 226 extending along the length of the sheath 210. In some embodiments, the tensile filament 226 may be disposed within a sheath lumen 225 formed within a circumferential wall 210A of the sheath 210. The tensile filament 226 may be formed of a metallic (e.g., Nitinol). In some embodiments, the tensile filament 226 may be a plastic filament, such as a nylon filament. As may be appreciated by one of ordinary skill, the tensile filament 226 may be formed of any medical grade material capable of providing a tensile force.

With reference to FIG. 2B, the tensile filament 226 may be threaded into an annular sleeve 227 extending circumferentially through a pliable segment wall 216A at a distal end of the pliable segment 216, entering the sleeve 227 at an entry point 227A. In some embodiments, the tensile filament 226 is disposed within the sleeve 227 along an entire circumference of the sheath 210. In other embodiments, the tensile filament 226 may be threaded through a plurality of segments of the sleeve 227. In still other embodiments, the tensile filament 226 may be threaded through holes extending through the pliable segment wall 216A.

A distal end of the tensile filament 226 is slidably coupled (e.g., via a slip knot) with the tensile filament 226 at the entry point 227A to form a cinching loop 228 of the tensile filament 226. As such, proximal displacement of the tensile filament 226 along the sheath lumen 225 causes the cinching loop 228 to tighten as further described below.

In some embodiments, the tensile filament 226 may include one or more pre-formed portions. For example, a distal portion of the tensile filament 226 may be formed into a loop shape so that the tensile filament 226 may define a radially outward directed force on the pliable segment 216 when the tensile filament 226 is disposed within the annular sleeve 227. In such an embodiment, the cinching loop 228 may help define the open configuration of the chamber 217.

With reference to FIG. 2C, the sheath assembly 200 includes a cinching actuator 212 operatively coupled with the tensile filament 226 at a proximal end of the tensile filament 226. In some embodiments, the tensile filament 226 may exit the sheath lumen 225 via a slot 225A. The cinching actuator 212 is configured for longitudinal displacement between a non-cinching position 212A and a cinching position 212B. In some embodiments, the cinching actuator 212 may be a rotational actuator configured to displace the tensile filament 226 in accordance with rotation of the actuator.

Figure 2D:
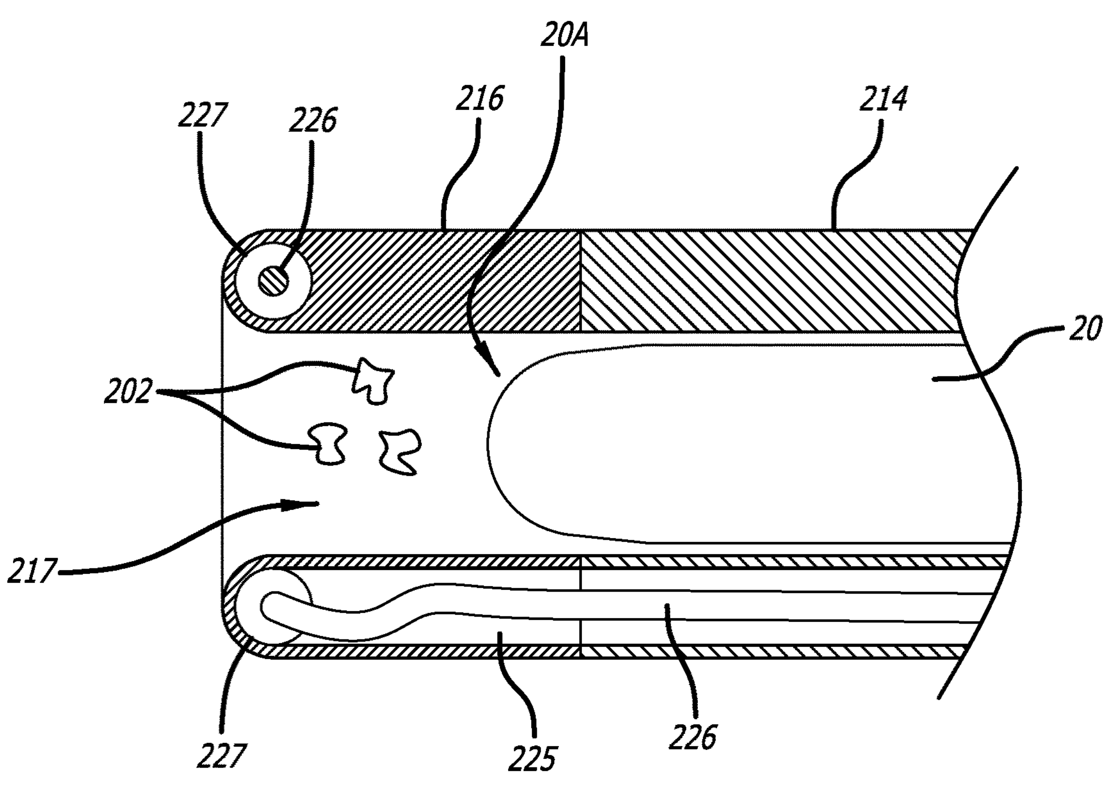
FIG. 2D is a cross-sectional detail view of the distal portion of the sheath assembly of FIG. 2A with the sheath assembly disposed in an extended position forming a chamber, in accordance with some embodiments.

FIG. 2D is a detail view of the distal portion similar to FIG. 2B with the sheath assembly 200 is disposed in the extended position. In the extended position, at least a portion of the pliable segment 216 extends beyond the distal end 20A of the shaft 20. As shown, the pliable segment 216 forms a chamber 217. In FIG. 2D, the chamber 217 is disposed in an open configuration consistent with the cinching actuator 212 disposed in the non-cinching position 212A (see FIG. 2C). In the open configuration, the chamber 217 allows for the placement of calculus pieces 202 to be disposed therein.

Figure 2E:
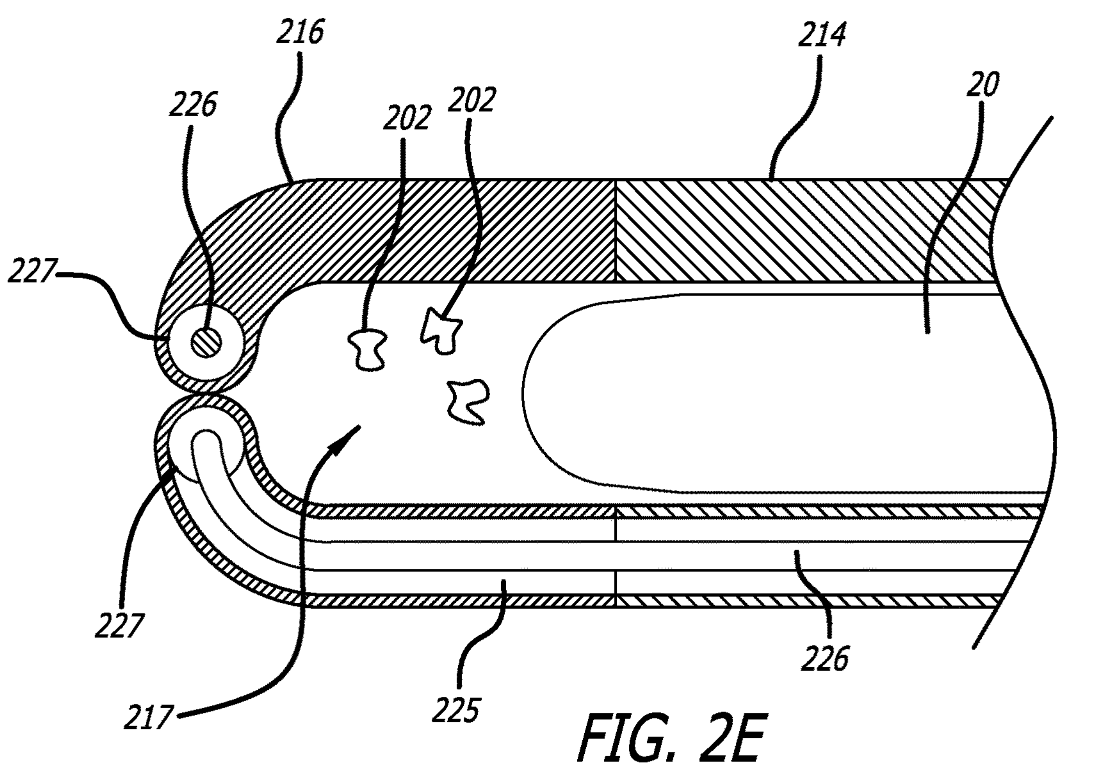
FIG. 2E is a cross-sectional detail view of the distal portion of the sheath assembly of FIG. 2A with the sheath assembly disposed in an extended position and the chamber disposed in a closed configuration, in accordance with some embodiments.

FIG. 2E is a detail view of the distal portion similar to FIG. 2D with the sheath assembly 200 is disposed in the extended position. FIG. 2E illustrates the chamber 217 in a closed configuration consistent with the cinching actuator 212 disposed in the cinching position 212B (see FIG. 2C). In other words, displacement of the cinching actuator 212 to the cinching position 212B pulls the tensile filament 226 proximally along the sheath 210 thereby tightening the cinching loop 228 to close off the open end of the chamber 217. With the chamber 217 disposed in the closed configuration, calculus pieces 202 contained within the chamber 217 may be removed from the patient upon extraction of the sheath assembly 200 from the patient.

Methods of using of the sheath assembly 200 may include the following steps or processes. The clinician may insert the shaft 20 of the endoscope 12 into the sheath 210 so that the pliable segment 216 is disposed proximal the distal end 20A. The clinician may insert the laser optical fiber 42 into the working channel 29 of the endoscope 12.

The clinician may insert a laser optical fiber 42 into the working channel 29 of the endoscope 12. The clinician may insert the shaft 20 of the endoscope 12 through the urethra and the bladder of the patient, and in some instances, into the ureter and/or kidney. The clinician may activate the articulation lever 32 to articulate the shaft 20 and thereby steer the distal tip 21 toward the desired location (e.g., the ureter). In doing so, the clinician may observe video images acquired by the video camera 27 to help guide the endoscope 12 and to visually detect a calculus (e.g., a kidney stone) to be removed. Upon detection, the clinician may activate the laser system 40 to break up the calculus into small pieces for removal. The clinician may displace the sheath assembly 200 distally along the shaft 20 to extend the pliable segment 216 of the sheath 210 beyond the distal end 20A forming the open-ended chamber 217. The clinician may manipulate the position of the endoscope 12 and/or the sheath assembly 200 to gather calculus pieces 202 into the chamber 217. The clinician may observe video images acquired by the video camera 27 to help gather calculus pieces 202 into the chamber 217. In some embodiments, the clinician may couple a fluid device (e.g., a syringe; not shown) to the fluid port 31A and apply a suction to the working channel 29 to urge the calculus pieces 202 into the chamber 217. The clinician may then activate the cinching actuator 212 (i.e., proximally displace the cinching actuator 212) to close off the chamber 217 and encapsulate the calculus pieces 202 within the closed chamber 217. The clinician may then retract the endoscope 12/sheath assembly 200 combination from the patient thereby removing the calculus pieces 202 from the patient. It is to be noted than any and all of the steps above may be performed with the laser optical fiber 42 disposed within the working channel 29. The clinician may remove the laser optical fiber 42 from the working channel 29.

FIGS. 3A-3G illustrates another embodiment of an endoscope 300. The endoscope 300 can, in certain respects, resemble components of the endoscope 12 in combination with the sheath assembly 200 described in connection with FIGS. 1A-2E. It will be appreciated that all the illustrated embodiments may have analogous features. Accordingly, like features are designated with like reference numerals, with the leading digit being "3." For instance, the shaft is designated as "20" in FIGS. 1A-2E, and an analogous shaft is designated as "320" in FIGS. 3A-3G. Relevant disclosure set forth above regarding similarly identified features thus may not be repeated hereafter. Moreover, specific features of the endoscope 12/sheath assembly 200 combination and related components shown in FIGS. 1A-2E may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the endoscope 300. Any suitable combination of the features, and variations of the same, described with respect to the endoscope 12/sheath assembly 200 combination and components illustrated in FIGS. 1A-2E can be employed with the endoscope 300 and components of FIGS. 3A-3G, and vice versa.

The endoscope 300 includes a cable 315 for coupling with a video control module. The laser optical fiber 42 may be inserted into the endoscope 300 via an access port 331. The access port 331 includes a fluid port 331A in fluid communication with the access port 331.

The endoscope 300 may include a flexible elongate shaft 320 having a rigid distal tip 321 at a distal end 320A. The shaft 320 may be attached to a handle 330 via a stain relief 323 at a proximal end 320B. The shaft 320 may include an articulating section 322 configured to articulate in opposing directions as shown. The articulating section 322 is operatively coupled with an articulation lever 332 disposed on the handle 330. The articulating section 322 is configured to articulate in accordance with actuation of the articulation lever 332.

The shaft 320 includes a sheath 310 disposed at the distal end 320A. The sheath 310 is slidably coupled with the rigid distal tip 321 so as to slide distally and proximally along the rigid distal tip 321. The sheath 310 is operatively coupled with a sheath displacement actuator 311 to define co-movement therewith as the sheath displacement actuator 311 is distally displaced as indicated by the arrow 311A as further described below. The sheath 310 is also operatively coupled with a cinching actuator 312 as also further described below. As indicated by the arrow 312A, the cinching actuator 312 is proximally displaceable with respect to the sheath displacement actuator 311.

Figure 3A:
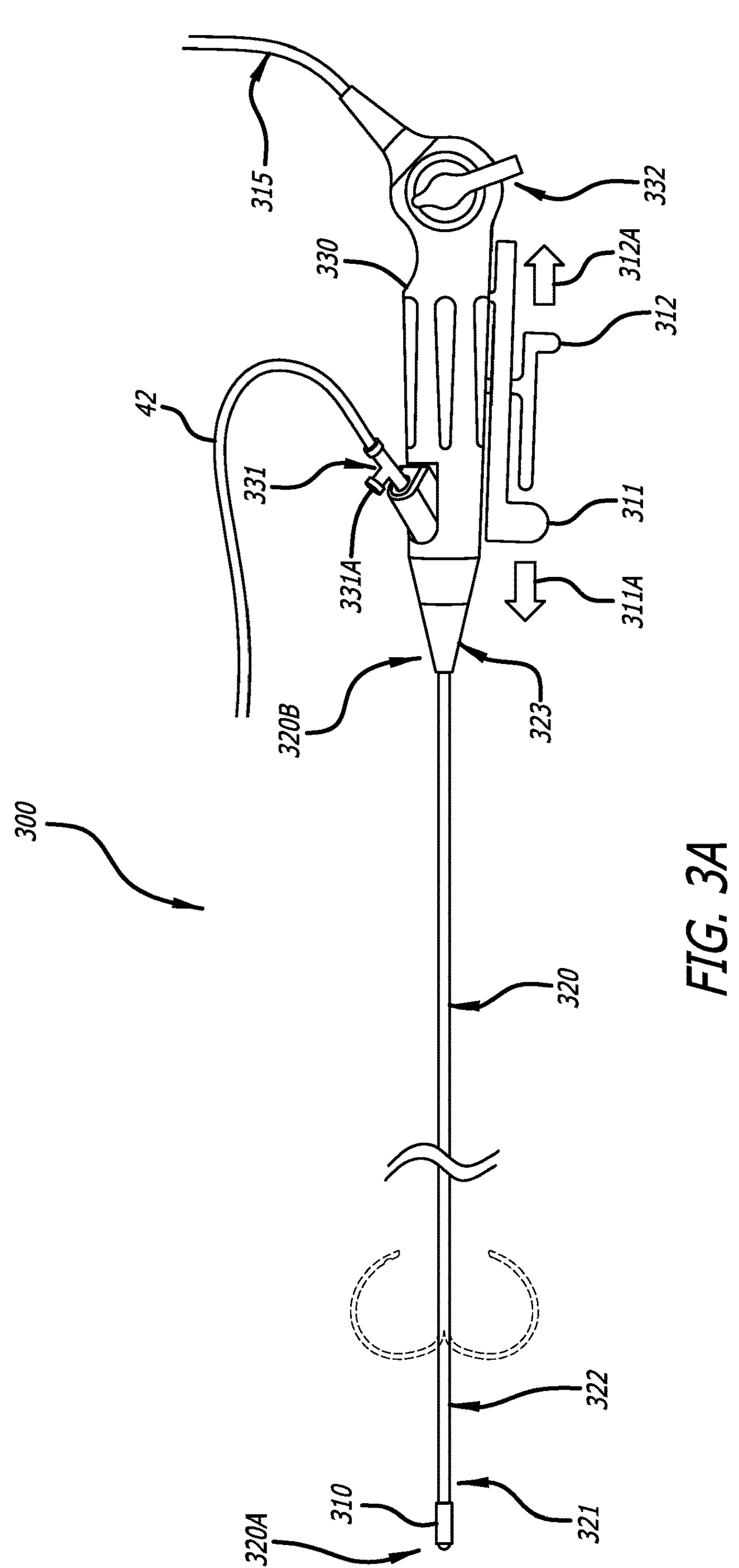
FIG. 3A is an illustration of an endoscope including a sheath, in accordance with some embodiments.
Figure 3B:
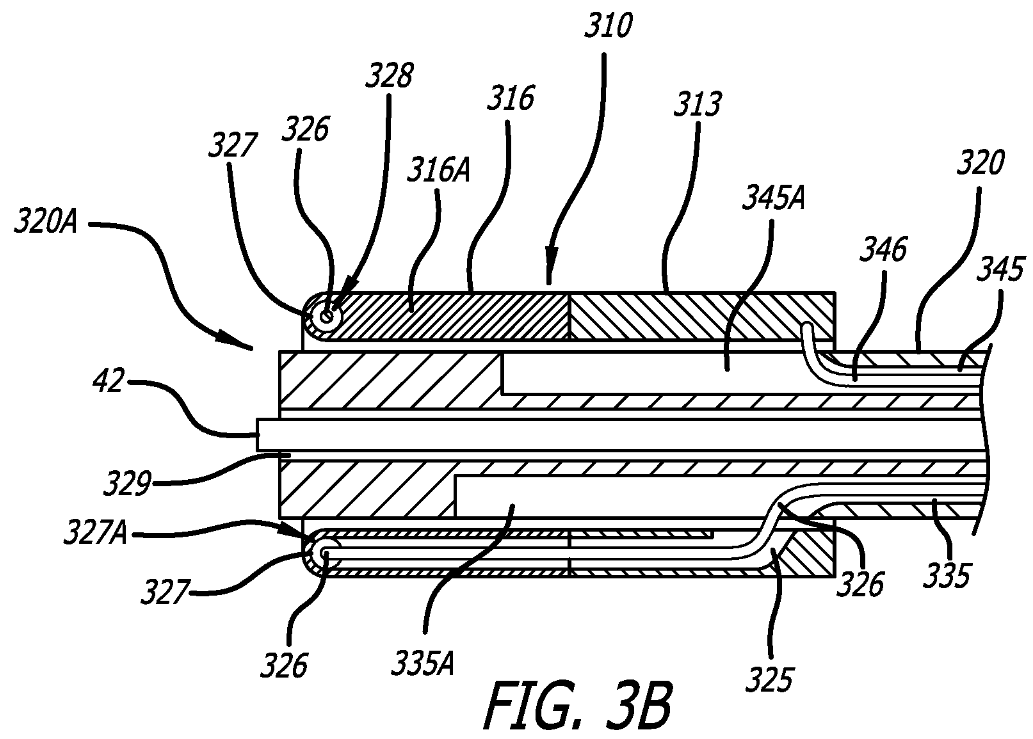
FIG. 3B is a cross-sectional detail view of a distal portion of the endoscope of FIG. 3A, in accordance with some embodiments.

FIG. 3B is a detail cross-sectional illustration of a distal portion of the shaft 320 including the sheath 310 disposed in a retracted position. The laser optical fiber 42 as may be disposed within the working channel 329 is shown for reference. The sheath 310 includes a pliable segment 316 attached to a tubular segment 313 proximal the pliable segment 316.

Figure 3C:
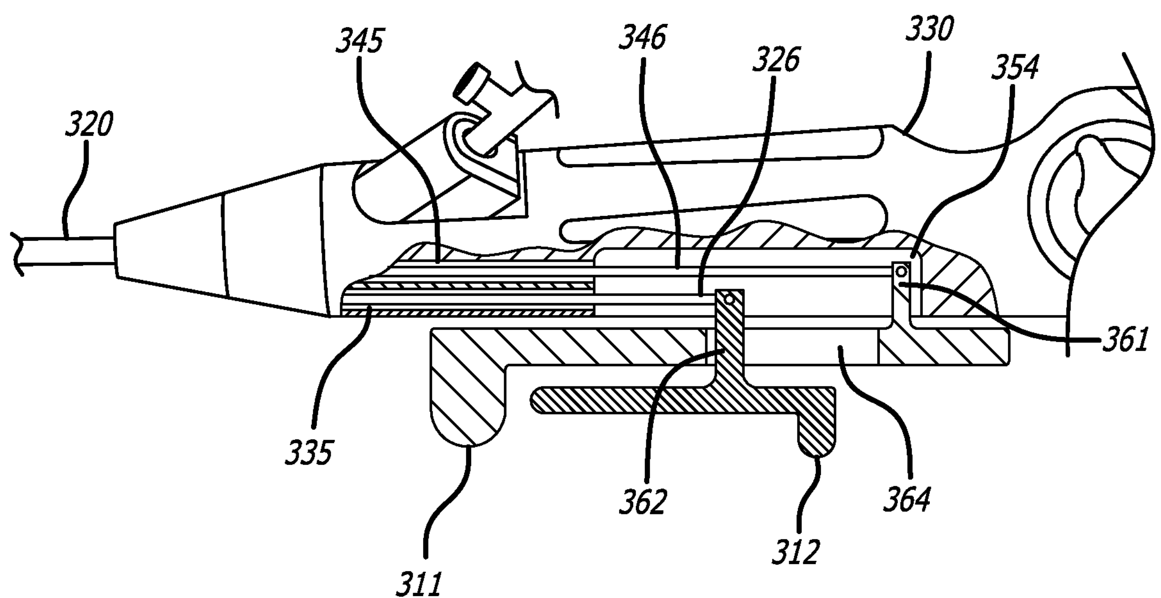
FIG. 3C is an illustration of a handle of the endoscope of FIG. 3A, in accordance with some embodiments.

FIG. 3C is a detail illustration of a portion of the handle 330 when the sheath 310 is in the retracted position. The endoscope 300 includes a sheath displacement wire 346 coupled between the sheath 310 (FIG. 3B) and the sheath displacement actuator 311. The sheath displacement wire 346 extends along the shaft 320, and in some embodiments, within a sheath displacement lumen 345. The sheath displacement actuator 311 may include a lateral extension 361 protruding into a handle slot 354 where it is attached to the sheath displacement wire 346. The handle slot 354 intersects the sheath displacement lumen 345. At the distal end 320A, the sheath displacement wire 346 exits the sheath displacement lumen 345 through a first sheath slot 345A.

With further reference to FIGS. 3B and 3C, a tensile filament 326 extends along the shaft 320 within a cinching lumen 335. The tensile filament 326 may be attached to the cinching actuator 312 via a lateral extension 362. The lateral extension 362 protrudes through a slot 364 in the sheath displacement actuator 311 and into the handle slot 354 where it is attached to the tensile filament 326. At the distal end 320A, the tensile filament 326 exits the cinching lumen 335 through a second sheath slot 335A at a proximal end of the slot 335A. The tensile filament 326 extends distally further along the sheath 310 through a sheath lumen 325 to a distal end of the sheath 310 at which point the tensile filament 326 bends (illustrated as into the page) to enter and extend through an annular circumferential sleeve 327 at the distal end of the sheath 310. The distal end of tensile filament 326 is slidably coupled to the tensile filament 326 at the location where the tensile filament 326 is threaded into an annular sleeve 327 extending circumferentially through a pliable segment wall 316A at a distal end of the pliable segment 316, entering the sleeve 327 at an entry point 327A. In some embodiments, the tensile filament 326 is disposed within the sleeve 327 along an entire circumference of the sheath 310. In other embodiments, the tensile filament 326 may be threaded through a plurality of segments of the sleeve 327. In still other embodiments, the tensile filament 226 may be threaded through holes extending through the pliable segment wall 316A. A distal end of the tensile filament 326 is slidably coupled (e.g., via a slip knot) with the tensile filament 326 at the entry point 327A to form a cinching loop 328 of the tensile filament 326. As such, proximal displacement of the tensile filament 326 along the sheath lumen 310 causes the cinching loop 328 to tighten as further described below.

Figure 3D:
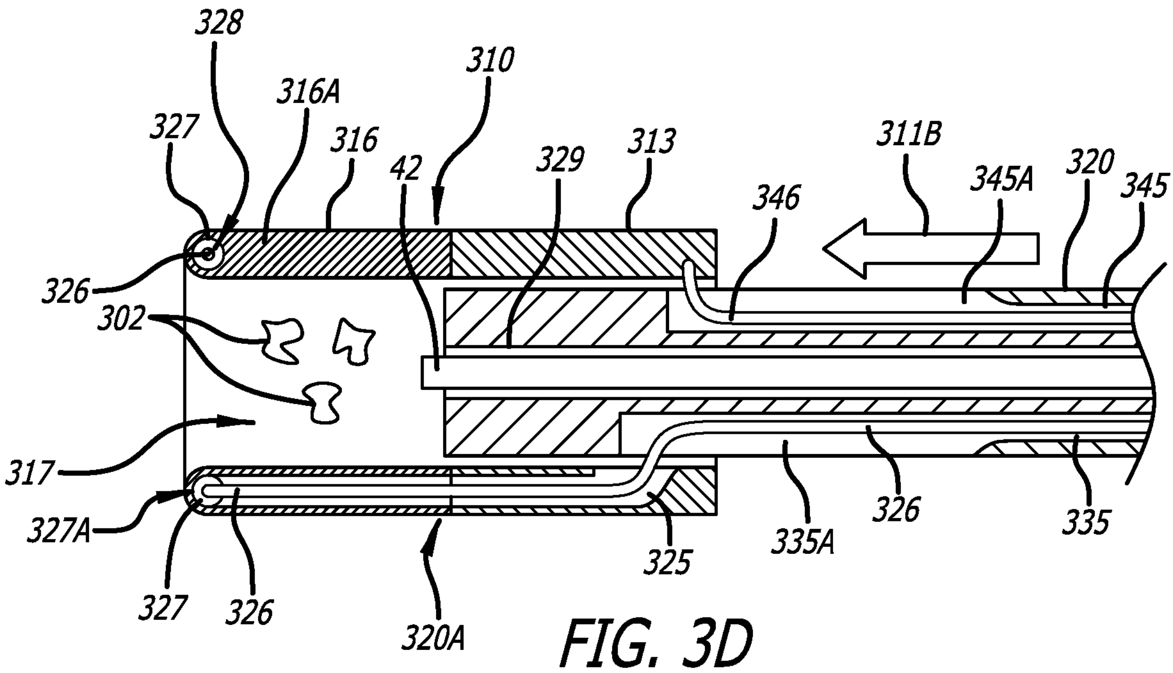
FIG. 3D is a cross-sectional detail view of the distal portion of the sheath assembly of FIG. 3A with the sheath assembly disposed in an extended position forming a chamber, in accordance with some embodiments.
Figure 3E:
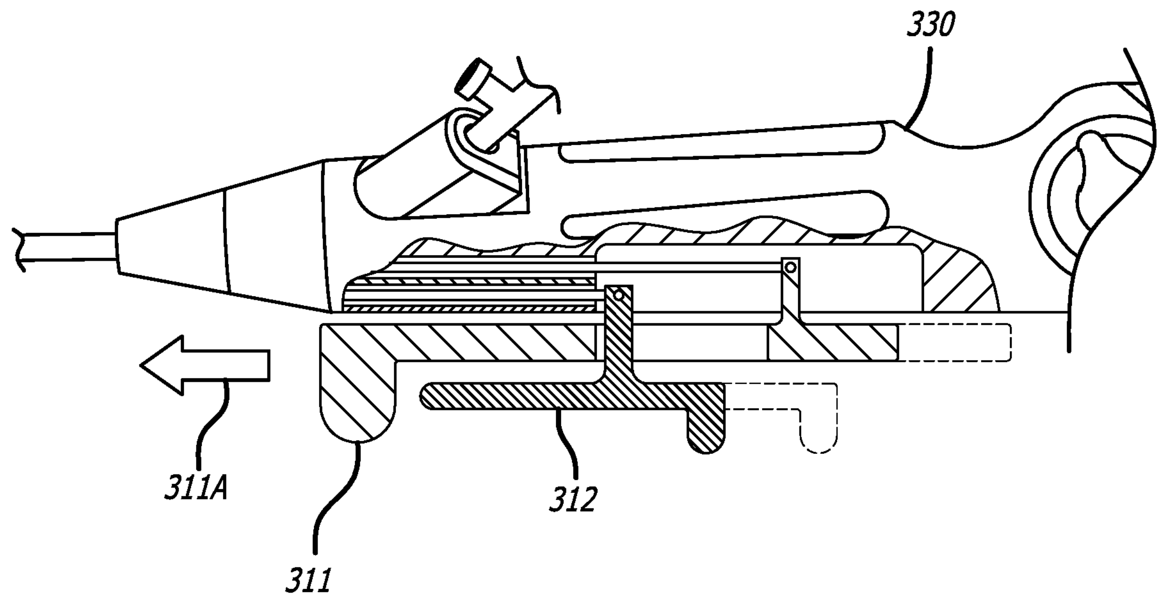
FIG. 3E is an illustration of the handle of the endoscope showing a sheath actuator disposed in a distal position consistent the extended position of the sheath of FIG. 3D, in accordance with some embodiments.

FIGS. 3D and 3E are similar views to FIGS. 3B and 3C with the sheath 310 disposed in an extended position. As shown in FIG. 3D the sheath 310 is distally displaced so that the pliable portion 316 of the sheath 310 extends beyond the distal end 320A thereby defining a chamber 317 in an open configuration. In the open configuration, the chamber 317 allows for the placement of calculus pieces 302 to be disposed therein. As shown in FIG. 3E, the sheath displacement actuator 311 is distally displaced in relation to the position shown in FIG. 3C as indicated by the arrow 311A. The cinching actuator 312 is also distally displaced together with the sheath displacement actuator 311 so that the chamber 317 remains in the open configuration.

Figure 3F:
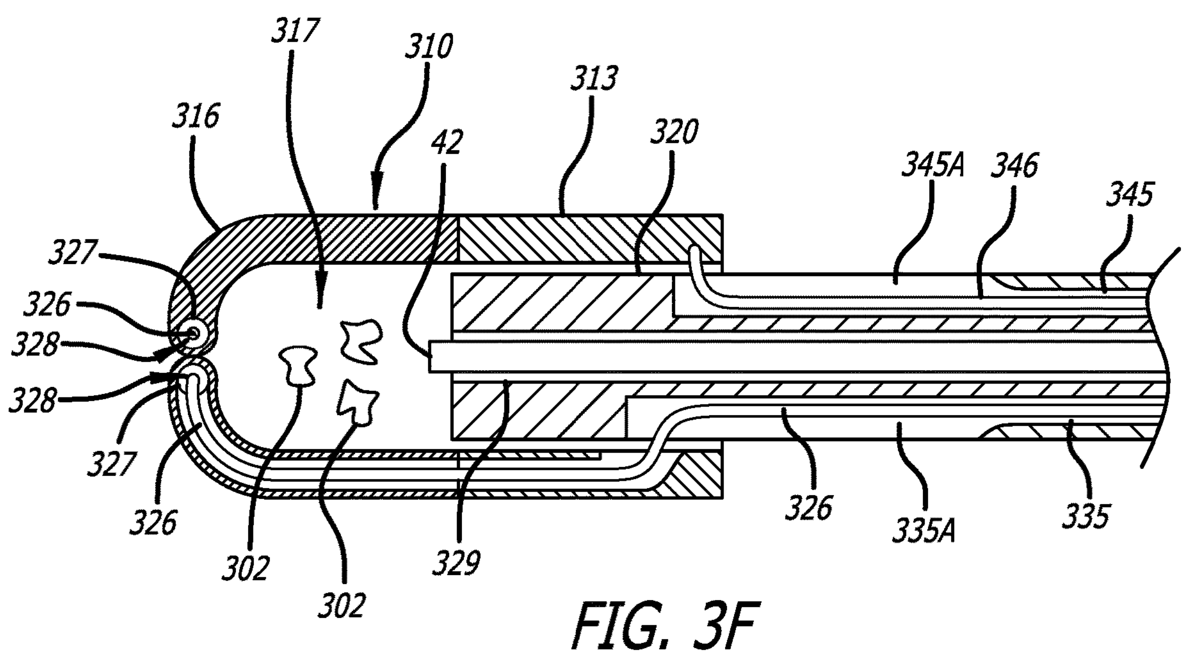
FIG. 3F is a cross-sectional detail view of the distal portion of the sheath assembly of FIG. 3A with the sheath assembly disposed in an extended position forming a chamber and the chamber disposed in a closed configuration, in accordance with some embodiments.
Figure 3G:
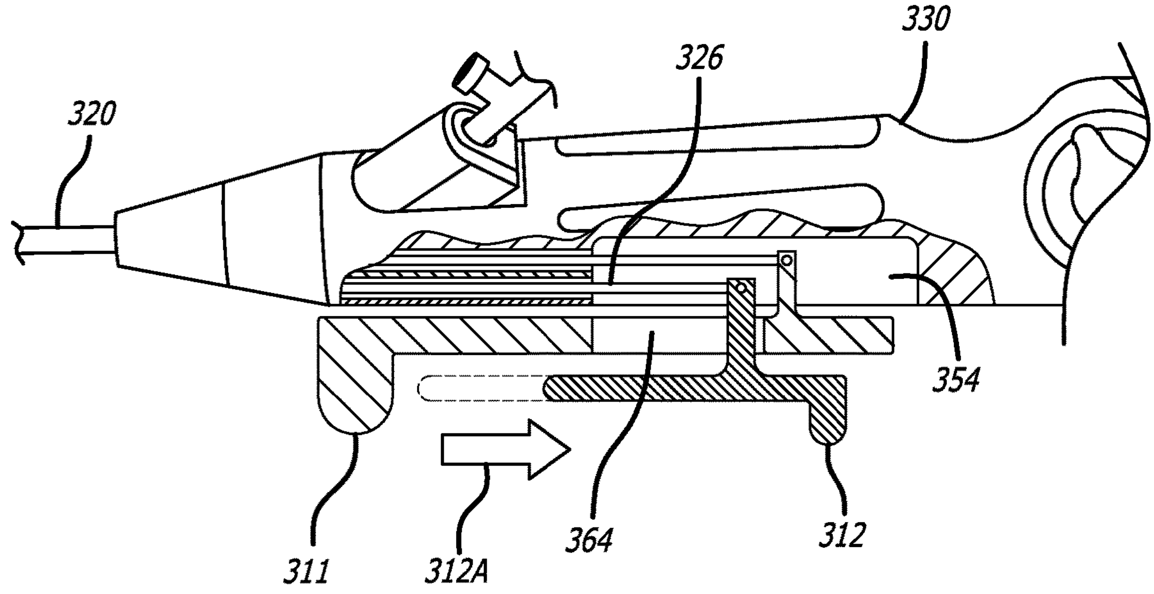
FIG. 3G is an illustration of the handle of the endoscope showing a cinching actuator disposed in a proximal position with respect to the sheath actuator consistent the chamber converted to the closed configuration, in accordance with some embodiments.

FIGS. 3F and 3G are similar views to FIGS. 3D and 3E with the sheath 310 disposed in the extended position. However, in FIG. 3G, the cinching actuator 312 is proximally displaced relative to the sheath displacement actuator 311 as indicated by the arrow 312A. The distal displacement of the cinching actuator 312 pulls tensile filament 326 distally along the shaft 320 and the sheath 310 to tighten the cinching loop 328 and thereby transition the chamber 317 from the open configuration (FIG. 3D) to a closed configuration (FIG. 3F) to encapsulate calculus pieces 302 within the chamber 317.

Methods of using of the endoscope 300 may include the following steps or processes. The clinician may insert a laser optical fiber 42 into the working channel 329 of the endoscope 300. The clinician may insert the shaft 320 of the endoscope 300 through the urethra and the bladder of the patient and further into the ureter and kidney. The clinician may activate the articulation lever 332 to articulate the shaft 320 and thereby steer the distal tip 321 toward the desired location. In doing so, the clinician may observe video images acquired by the video camera 27 to help guide the endoscope 300 and to visually detect a calculus to be removed. Upon detection of the calculus, the clinician may activate the laser system 40 to break up the calculus into small pieces for removal. The clinician may activate the sheath displacement actuator 311 to distally extend the sheath 310 so that the pliable segment 316 extends beyond the distal end 320A forming the open-ended chamber 317. The clinician may manipulate the position of the endoscope 300 and/or the sheath 310 to gather calculus pieces 302 into the chamber 317. The clinician may observe video images acquired by the video camera 27 to help gather calculus pieces 302 into the chamber 317. In some embodiments, the clinician may couple a fluid device (e.g., a syringe; not shown) to the fluid port 331A and apply a suction to the working channel 329 to urge the calculus pieces 302 into the chamber 317. The clinician may then activate the cinching actuator 312 (i.e., proximally displace the cinching actuator 312) to close off the chamber 317 and encapsulate the calculus pieces 302 within the closed chamber 317. The clinician may then retract the endoscope 300 from the patient thereby removing the calculus pieces 302 from the patient. It is to be noted than any and all of the steps above may be performed with the laser optical fiber 42 disposed within the working channel 329. The clinician may remove the laser optical fiber 42 from the working channel 329.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A sheath assembly for use with an endoscope, comprising:

an elongate tubular sheath configured to thread onto an elongate shaft of the endoscope, the elongate tubular sheath comprising a pliable segment at a distal end of the elongate tubular sheath; and a tensile filament extending along a circumference of the pliable segment to form a cinching loop at a distal end of the pliable segment, the tensile filament further extending proximally along the elongate tubular sheath, wherein:

the elongate tubular sheath is displaceable along the endoscope between a retracted position and an extended position, a distal end of the endoscope extends distally beyond the pliable segment in the retracted position, the pliable segment extends distally beyond the distal end of the endoscope in the extended position to form a chamber, proximal displacement of the tensile filament tightens the cinching loop to convert the chamber from an open configuration to a closed configuration, the elongate tubular sheath includes:

a sheath wall extending circumferentially around the chamber, the sheath wall defining an inside surface and an outside surface; and a filament lumen extending longitudinally along the sheath wall, the filament lumen disposed within the sheath wall between the inside surface and the outside surface, and a distal portion of the tensile filament is entirely disposed within the filament lumen, the distal portion extending longitudinally along the pliable segment.

2. The assembly according to claim 1, wherein the endoscope is a ureteroscope.

3. The assembly according to claim 1, wherein the sheath assembly is configured for insertion into a kidney of a patient body.

4. The assembly according to claim 1, wherein the sheath assembly is configured for removal of a calculus or portions thereof from a patient.

5. The assembly according to claim 1, wherein the sheath assembly is configured for removal of a calculus or portions thereof while a laser optical fiber is disposed within a working channel of the endoscope.

6. The assembly according to claim 1, wherein the tensile filament extends proximally along the elongate shaft of the endoscope toward a handle of the endoscope.

7. The assembly according to claim 1, wherein a loop portion of the tensile filament is at least partially disposed within an annular sleeve of the pliable segment.

8. The assembly according to claim 1, wherein a proximal portion of the tensile filament is disposed within a longitudinal lumen of the elongate tubular sheath.

9. The assembly according to claim 1, wherein the sheath extends proximally along the shaft of the endoscope toward a handle of the endoscope.

10. The assembly according to claim 1, further comprising an actuator operatively coupled with the tensile filament, the actuator configured for manual manipulation between a first position and a second position, wherein:

the chamber is disposed in the open configuration when the actuator is in the first position, and the chamber is converted to the closed configuration when the actuator is manipulated to the second position.

11. The assembly according to claim 10, wherein the actuator is a slidable actuator configured for manual manipulation between a distal first position and a proximal second position.

12. The assembly according to claim 1, wherein the tensile filament comprises a pre-formed loop shape.

13. The assembly according to claim 1, wherein the tensile filament comprises a metallic wire.

14. The assembly according to claim 1, wherein:

the elongate tubular sheath comprises an elongate main segment extending distally away from a proximal end of the elongate tubular sheath, and the elongate main segment is configured to flex in accordance with the elongate shaft of the endoscope.

15. The assembly according to claim 14, wherein an actuator is coupled with the elongate main segment.

16. The assembly according to claim 14, wherein:

the elongate tubular sheath comprises an articulating segment disposed between the elongate main segment and the pliable segment, and the articulating segment is configured to articulate in accordance with an articulating section of the elongate shaft of the endoscope.

17. An endoscope system, comprising:

the endoscope having the elongate shaft; and the sheath assembly according to claim 1, wherein the sheath assembly is coupled with the elongate shaft of the endoscope.

* * * * *